(12) United States Patent
Bucina

(10) Patent No.: US 7,458,979 B2  
(45) Date of Patent: Dec. 2, 2008

(54) INTERNAL TIP SEAL FOR ATTACHMENT/MOTOR FOR SURGICAL INSTRUMENTS

(75) Inventor: Stephen M. Bucina, Hobe Sound, FL (US)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 365 days.

(21) Appl. No.: 11/038,948

(22) Filed: Jan. 18, 2005

(65) Prior Publication Data

US 2006/0161191 A1    Jul. 20, 2006

(51) Int. Cl.
- A61B 17/32    (2006.01)
- B23B 31/117   (2006.01)
- B25G 3/22     (2006.01)

(52) U.S. Cl. .................. 606/180; 408/226; 279/157
(58) Field of Classification Search .......... 606/180, 606/80; 403/307; 279/157, 99; 408/226, 408/171

See application file for complete search history.

(56) References Cited

U.S. PATENT DOCUMENTS

| | | | | |
|---|---|---|---|---|
| 1,378,015 A | * | 5/1921 | Erickson | 285/39 |
| 3,674,075 A | * | 7/1972 | Hoegee | 411/277 |
| 4,071,029 A | * | 1/1978 | Richmond et al. | 606/180 |
| 6,358,252 B1 | * | 3/2002 | Shapira | 606/80 |
| 6,974,436 B1 | * | 12/2005 | Aboul-Hosn et al. | 604/9 |
| 2001/0052276 A1 | * | 12/2001 | Riedl et al. | 81/429 |

* cited by examiner

*Primary Examiner*—Todd E Manahan  
*Assistant Examiner*—Jocelin C Tanner  
(74) *Attorney, Agent, or Firm*—Norman Friedland

(57) ABSTRACT

A seal for an attachment to a surgical motor is provided by cutting threads into the inner surface of the nose cone of the attachment whereby the helical wound threads are in a direction opposite to the direction of the rotating shaft of the instrument being supported by the attachment. The motor can likewise by configured to define a seal where an attachment is not being utilized.

9 Claims, 2 Drawing Sheets

INTERNAL TIP SEAL FOR ATTACHMENT/MOTOR FOR SURGICAL INSTRUMENTS

FEDERALLY SPONSORED RESEARCH

None

TECHNICAL FIELD

This invention relates to surgical drills and attachments and more particularly to sealing the attachment shaft of the surgical instrument to prevent the inclusion of foreign matter internally in the drill/attachment.

BACKGROUND OF THE INVENTION

As is well known in this technology, an attachment mechanism is typically added to the surgical motor and provides an extension thereof and includes bearings to support the shaft extending through the attachment mechanism which shaft carries surgical tools such as cutters, cutting burrs, and the like. One of the problems with these attachment mechanism is that they have the propensity that allows foreign matter to migrate inwardly internal of the attachment mechanism and not only can foul up the bearings supporting the shaft but can otherwise contaminate the attachment and/or the motor. Obviously, when employed in performing a medical procedure, as for example, open surgery, partial open surgery, arthroscopic surgery and the like, it is imperative that the attachment and the motor remain free from foreign matters and contamination.

I have found that by the judicial thread configuration formed internally at the end of the attachment or motor case, foreign matter like bone particles, dust and the like, are prohibited from entering the internal portion of the drill/attachment and hence, prevents contamination or damage thereto.

SUMMARY OF THE INVENTION

An object of this invention is to provide improved sealing means for the attachment and/or drill used for surgical procedures.

A feature of this invention is to configured the inner diameter at the tip of the attachment/drill to include teeth that are oriented in a direction opposite to the direction of the rotating shaft. In an attachment configuration, the nose cone is designed with the teeth so that the teeth are located just upstream of the bearing relative to the forward end of the instrument.

The foregoing and other features of the present invention will become more apparent from the following description and accompanying drawings.

These figures merely serve to further clarify and illustrate the present invention and are not intended to limit the scope thereof.

DETAILED DESCRIPTION OF THE INVENTION

The primary objective of this invention is to prevent the inclusion of foreign bodies to migrate into the inner portion of an attachment of the type used for supporting rotating instruments such as burrs, drills and the like that are attached to a motor for driving the rotating instruments that is utilized in surgical procedures. The attachment typically includes bearings to rotary support the shaft of the working instruments, but as one skilled in this art will appreciate the invention can be equally applied directly to the motor where no attachment is being utilized.

Figure 1:
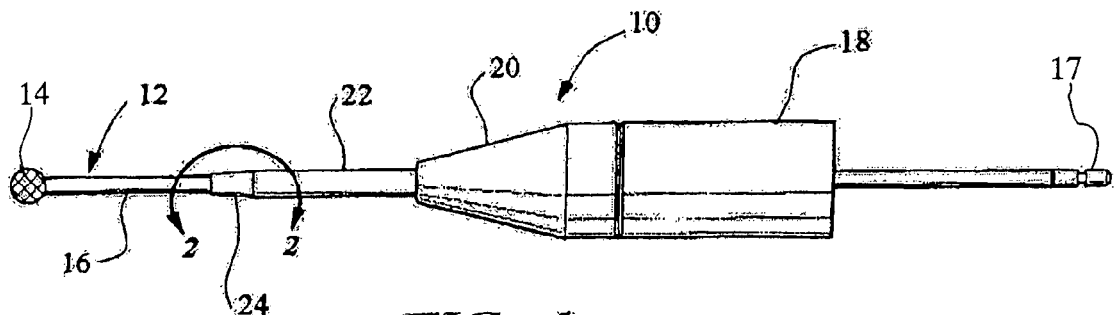
FIG. 1 is a view in elevation view of a prior art attachment for rotary support of a cutter tool for use in medical procedures illustrating this invention.
Figure 2:
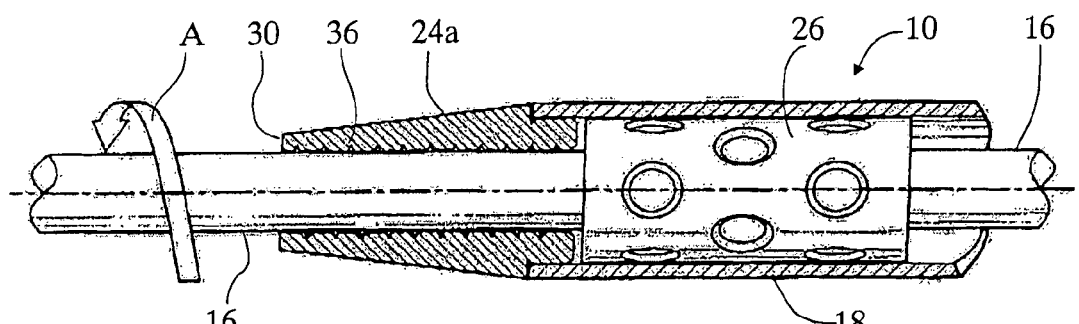
FIG. 2 is an enlarged view of a portion of a modified version of the embodiment depicted in FIG. 1 taken along the lines 2-2 illustrating the seal of this invention configured in the nose cone of the attachment instrument.
Figure 3:
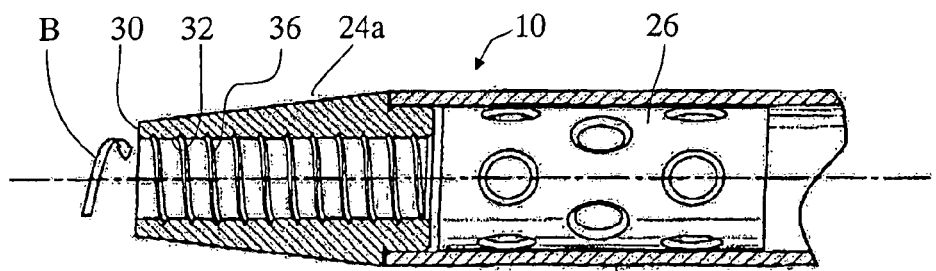
FIG. 3 is a sectional view of the modified version of the attachment as depicted in FIG. 2 with the cutting tool removed therefrom.

As best seen in FIGS. 1, 2 and 3, the typical and heretofore commercially available attachment, available, for example, from the assignee of the present invention, generally illustrated as reference numeral 10 and a cutting tool generally illustrated by reference numeral 12. The attachment 10 comprises an outer housing 18 that is tubular shaped, a reduced diameter portion 22 fairing toward the center line of the attachment, and a nose cone 20 fairing into an even further reduced diameter at the distal end 16 attached to the distal end of housing 18. The attachment, although not a part of the invention, typically includes suitable bearing 26 (the balls are omitted from the circular pockets) and chuck mechanism that serves to attach the attachment to a suitable motor, (not shown). The distal portion of the attachment is designed to be sufficiently small in diameter to allow the surgeon to comfortably hold the attachment/motor so as to perform the medical procedure with the rotating working element and provide good visual characteristics to the working area where the surgeon is performing a medical procedure.

The cutter, generally illustrated by reference numeral 12 comprises the spherical shaped cutter bit 14, shaft 16 that extends beyond the attachment 10 and fits into the motor (not shown). These portions of the medical instrument are well known and for the sake of convenience and simplicity a description thereof is being omitted herefrom. Suffice it to say that the removable cutting tool extends through the attachment 10, is held therein by a suitable chuck and is driven by a suitable motor. As noted the proximal end includes an annular groove and shape identified by reference numeral 17 for engaging the chuck of the motor (not shown).

Figure 4:
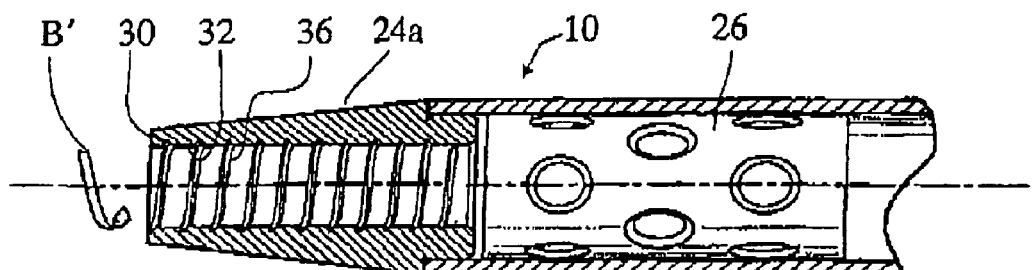
FIG. 4 is a sectional view identical to the device depicted FIG. 3 showing the helical threads in the reverse position to accommodate a rotary machine that has a rotary motion that is opposite to the rotary motion of the device depicted in FIG. 3.
Figure 5:
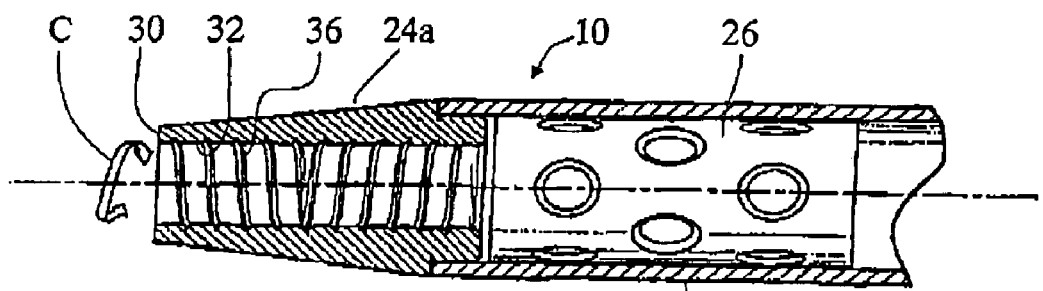
FIG. 5 is a sectional view identical to the device depicted in FIG. 4 illustrating helical threads wound in opposite directions to accommodate a rotary machine that rotates in a forward and a reverse direction.

In this installation a nose cone 24 is suitably attached to the end of the tubular casing member 16 and fairs to a reduced diameter end portion 30 and includes a central bore 32 through which the shaft 16 of the cutter passes through. In accordance with this invention, the inner diameter of the nose cone 28 is configured with an helical wound thread 36 whose depth, pitch diameter, pitch, major and minor diameters are not critical but the dimensions of which are selected to assure that foreign matter will not migrate inwardly toward the proximal end of the attachment, and particularly away from the bearings. Of importance, however, is that the orientation of the threads are selected so that they are in the opposite direction of the rotation of the cutter. For example, if the cutter is rotating clockwise (arrow A), the direction of the threads will be counter clockwise (arrow B) as shown in FIG. 3, and vice versa as shown in FIG. 4. in other words, where the cutter rotates in the clockwise direction, the threads will be left handed threads. This does not negate the possibility that the threads can be double threads so that a portion of the threads are left handed and the remaining portion are right handed which may be desirable in the event a reversing motor is utilized as shown in FIG. 5.

Although this invention has been shown and described with respect to detailed embodiments thereof, it will be appreciated and understood by those skilled in the art that various changes in form and detail thereof may be made without departing from the spirit and scope of the claimed invention.

It is claimed:

1. A removable attachment of the type that supports a unidirectional rotating cutting instrument used in a medical procedure by a surgeon including a tubular outer housing having a distal end, a bearing for supporting the shaft of the rotating instrument, a chuck on the tubular outer housing for connecting the removable attachment to a motor rotating said shaft in said unidirection, the improvement consisting essentially of a helically wound groove formed an inner diametrical surface tubular outer housing and being adjacent to and in proximity to the distal end, and the direction of the helical groove being opposite the direction of the rotation of the shaft so as to prevent the inclusion of foreign matter internally.

2. The improvement as claimed in claim 1 wherein the outer housing includes a nose cone at the distal end thereof, said groove being formed in said nose cone and being adjacent to and in proximity to the distal end.

3. The improvement as claimed in claim 2 wherein the groove is in the axial extent of said nose cone.

4. A removable attachment of the type that supports a rotating instrument used in a medical procedure by a surgeon including a tubular outer housing having a distal end, a bearing for supporting the shaft of the rotating instrument, a chuck on the tubular outer housing for connecting the removable attachment to a motor rotating said shaft, the improvement consisting essentially of helically wound grooves formed in an inner diametrical surface of tubular outer housing and being adjacent to and in proximity to the distal end, one of said helical wound grooves being in a clockwise direction and the other of said helical wound grooves being in the counterclockwise direction and the direction of the said one helical wound grooves or said other helical grooves being opposite to the direction of the rotation of the shaft so as to prevent the inclusion of foreign matter internally notwithstanding the direction of rotation of said shaft.

5. The improvement as claimed in claim 4 wherein the outer housing includes a nose cone at the distal end having an inner surface, said helically wound grooves being formed in said inner surface of said nose cone and being adjacent to and in proximity to said shaft.

6. The improvement as claimed in claim 5 wherein the grooves extend the axial extent of said nose cone.

7. In combination, a removable attachment of the type that supports a unidirectional rotating cutting instrument used in a medical procedure by a surgeon including a tubular outer housing having an inner surface having a distal end, a bearing for supporting the shaft of the rotating instrument, a chuck on the tubular outer housing for connecting the removable attachment to a motor rotating said shaft in said unidirection, said inner surface having a helically wound groove formed therein and being adjacent to and in proximity to the distal end, and the direction of the helical groove being opposite to the direction of the rotation of the shaft so as to prevent the inclusion of foreign matter internally of said removable attachment.

8. The combination as claimed in claim 7 wherein the outer housing includes a nose cone at the distal end thereof, said groove being formed in said nose cone and being adjacent to and in proximity to the distal end.

9. The combination as claimed in claim 8 wherein said groove is in the axial extent of said nose cone.

* * * * *